(12) United States Patent
Jones (10) Patent No.: US 8,323,187 B2
(45) Date of Patent: Dec. 4, 2012

(54) NONINVASIVE MEDICAL DEVICE AND METHOD OPERABLE IN A LIMITED AMOUNT OF TIME THROUGH A DELIBERATE HUMAN MOTION

(75) Inventor: Zach Jones, Half Moon Bay, CA (US)

(73) Assignee: Black Mountain Ventures, Pierre, SD (US)

( * ) Notice: Subject to any disclaimer, the term of this patent is extended or adjusted under 35 U.S.C. 154(b) by 1111 days.

(21) Appl. No.: 12/233,608

(22) Filed: Sep. 19, 2008

(65) Prior Publication Data

US 2010/0076507 A1    Mar. 25, 2010

(51) Int. Cl.
*A61B 5/02*    (2006.01)

(52) U.S. Cl. .................. 600/300; 600/310; 600/509

(58) Field of Classification Search ............ 607/35; 362/192–193; 310/12.01–12.33
See application file for complete search history.

(56) References Cited

U.S. PATENT DOCUMENTS

| | | | | |
|---|---|---|---|---|
| 5,347,186 | A * | 9/1994 | Konotchick | 310/17 |
| 5,535,853 | A * | 7/1996 | Skalski | 187/410 |
| 5,818,132 | A | 10/1998 | Konotchick | |
| 5,876,351 | A | 3/1999 | Rohde | |
| 5,975,714 | A | 11/1999 | Vetorino et al. | |
| 6,220,719 | B1 * | 4/2001 | Vetorino et al. | 362/192 |
| 6,556,867 | B1 | 4/2003 | Kohls | |
| 6,768,230 | B2 | 7/2004 | Cheung et al. | |
| 6,798,090 | B2 | 9/2004 | Cheung et al. | |
| 6,809,427 | B2 | 10/2004 | Cheung et al. | |
| 6,812,583 | B2 | 11/2004 | Cheung et al. | |
| 6,812,598 | B2 | 11/2004 | Cheung et al. | |
| 6,833,780 | B2 | 12/2004 | Cheung | |
| 6,861,772 | B2 | 3/2005 | Cheung et al. | |
| 6,917,131 | B2 | 7/2005 | Cheung | |
| 7,009,310 | B2 | 3/2006 | Cheung et al. | |
| 7,148,583 | B1 * | 12/2006 | Shau et al. | 290/1 R |
| 7,498,682 | B2 * | 3/2009 | Lemieux | 290/1 R |
| 8,221,439 | B2 * | 7/2012 | Dlugos et al. | 606/151 |
| 2004/0152953 | A1 * | 8/2004 | Goedeke | 600/300 |
| 2007/0276270 | A1 * | 11/2007 | Tran | 600/508 |
| 2008/0074083 | A1 * | 3/2008 | Yarger et al. | 320/137 |
| 2008/0091089 | A1 * | 4/2008 | Guillory et al. | 600/301 |
| 2009/0079200 | A1 * | 3/2009 | Gieras et al. | 290/1 R |
| 2009/0146508 | A1 * | 6/2009 | Peng et al. | 310/15 |
| 2009/0247850 | A1 * | 10/2009 | Porges | 600/323 |

FOREIGN PATENT DOCUMENTS

WO    WO-2006131770 A3    12/2006

* cited by examiner

*Primary Examiner* — Carl H Layno
*Assistant Examiner* — Luther Behringer
(74) *Attorney, Agent, or Firm* — Kilpatrick Townsend & Stockton LLP (57) ABSTRACT

A method, system, and apparatus of a medical device powered by deliberate human motion for limited use are disclosed. In one embodiment, a medical device includes a motion module to sense whether a deliberate human motion is convertible to an electric current to power the medical device, a power module to convert the deliberate human motion to a limited use electric current that enables the medical device to operate during a limited cycle of time, and an energy storage module to store the limited use electric current converted from the deliberate human motion. The medical device may include a power sensing module to determine whether a threshold amount of energy has been generated. The medical device may also include a sensor of the motion module to sense whether the deliberate human motion is convertible to the limited use electric current by permitting a physical object to oscillate.

14 Claims, 10 Drawing Sheets

NONINVASIVE MEDICAL DEVICE AND METHOD OPERABLE IN A LIMITED AMOUNT OF TIME THROUGH A DELIBERATE HUMAN MOTION

FIELD OF TECHNOLOGY

This disclosure relates generally to an enterprise method, a technical field of software and/or hardware technology and, in one example embodiment, to a noninvasive spectroscopic medical device powered for a limited period of time by deliberate human motion.

BACKGROUND

A medical device (e.g., a pulse oximeter, an electrocardiogram (ECG), an automated external defibrillator (AED), a glucometer, etc.) may require an electric current to operate. A battery (e.g., an alkaline battery, a lithium ion/lithium polymer battery, a nickel metal hydride battery, a lead acid battery, etc.) may supply electricity to the medical device. Over time, the battery may experience problems (e.g., an electrolyte of the battery may freeze or evaporate, excessive amounts of lead sulphate may form at a terminal of the battery, electrolytic fluids may permeate through battery seals and/or separator films, pressure may build up as a result of evolved product gases, etc.) resulting in battery failure and/or self discharge.

Misuse and/or improper storage of the battery (e.g., overcharging the battery, allowing accidental shorts to occur between terminals, excessive storage time prior to use, storing the battery at a temperature outside the manufacturer specified range, etc.) may also cause it to lose capacity over time. Furthermore, each purchase of a new battery for a medical device may add cost to the medical treatment provided. Disposal of a toxic material within the battery may also add additional cost. If improperly discarded, the toxic material of the battery could become a health risk.

In addition, in certain areas and/or countries (e.g., developing countries, conflict regions, disaster areas, remote regions, areas with infrequent supply shipments, etc.) delivery of replacement batteries may be interrupted. Delivery costs in some situations (e.g., remote regions, disaster areas, rush deliveries, restricted access areas, etc.) may also add to the cost of medical treatment. As a result, a battery powered medical device may not work in many scenarios.

SUMMARY

A method, system, and apparatus of a medical device operable in a limited amount of time through a deliberate human motion are disclosed. In one aspect, a medical device includes a power module to convert the deliberate human motion to an electric current which enables the medical device to operate during a limited period of time, and an energy storage module to store the electric current converted from the deliberate human motion.

The medical device may include a power sensing module to determine whether a threshold amount of energy has been generated and stored. The medical device may also include a motion module to sense whether a deliberate human motion is convertible to an electric current to power the medical device. The motion module may be comprised of the physical components of the power module. In addition, the medical device may include a sensor of the motion module to sense whether the deliberate human motion is convertible to the electric current by permitting a physical object to oscillate. The medical device may also include a magnet of the power module to convert the deliberate human motion to the electric current by moving through a fixed path in relation to a conductor. The medical device may include a coil oriented in a plane such that a magnet oscillating in a parallel plane is able to convert the deliberate human motion to the electric current. In addition, the medical device may include a coil of the conductor of the power module (e.g., such that the magnet may be able to oscillate through the coil of the conductor to convert the deliberate human motion to an electric current).

The medical device may also include an axis of the power module (e.g., such that the magnet may be able to orbit the axis with relation to a fixed conductor to convert the deliberate human motion to an electric current). The deliberate human motion may be a shaking motion that causes the magnet of the power module to oscillate in relation to the conductor to convert the deliberate human motion to an electric current. Operation of the medical device during the limited period of time may be a single use of the medical device (e.g., such that it may be usable one time before discharging the energy storage module). A power converted from the deliberate human motion may be stored in a capacitance within the energy storage module.

The medical device may include a spectroscopic sensor powered by the electric current from the deliberate human motion, (e.g., the spectroscopic sensor may be a pulse oximeter and/or a glucometer). Operating the medical device may perform an oxygen saturation reading, a heart rate reading and/or a blood glucose level reading. The medical device may include a port for an other sensor powered for the limited period of time by an energy converted from the deliberate human motion. The medical device may also include a notification module using an audible tone, a vibration, and/or a visual signal to notify a user that the electric current converted from the deliberate human motion has reached a threshold level. In addition, the medical device includes a display powered by the electric current from the deliberate human motion to display information associated with data captured during the limited period of time the medical device is operational.

The medical device may also include a rectification module to modify the electric current to be stored in the energy storage module. The medical device may include a restrictor module to prevent the deliberate human motion from being converted into the electric current by limiting a motion of a magnet and a conductor. In addition, the method may include a base unit to provide a constant electric current to allow continuous use of the medical device and/or to hold the medical device in a preferred position. The energy storage module may also be able to store the electric current from a hand crank, an external battery, a solar cell, a commercially available mains power (e.g., electricity from a power grid), a fossil fuel powered generator, and/or a wind generator to operate the medical device during the limited period of time.

A method may include sensing a deliberate human motion with a motion module, converting the deliberate human motion to an electric current with a power module to operate a medical device during a limited period of time, storing the electric current converted from the deliberate human motion in an energy storage module, determining whether a threshold amount of an energy has been stored in the energy storage module to permit the medical device to operate during a limited period of time, discharging the energy in the energy storage module to operate the medical device for limited period of time.

Another method may include forming a power module in the medical device to convert a deliberate human motion to the electric current for a limited use of the medical device, and placing an energy storage module in the medical device to store the electric current converted from the deliberate human motion for the limited use of the medical device. The method may also include creating a motion module in a medical device to sense whether a human motion is convertible to an electric current to power the medical device, and forming a physical object internal to the medical device to sense the deliberate human motion by observing a motion of the physical object. The method of creating the power module in the medical device may also form the motion module and the physical object internal to the medical device to sense the deliberate human motion. The method may further include placing a magnet of the power module in the medical device to convert the deliberate human motion into the electric current by moving the magnet in relation to a conductor. The method may create a pulse oximeter in the medical device to perform a pulse oximetry reading consisting of a heart rate data and/or an oxygen saturation data.

The methods, systems, and apparatuses disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

A method, system, and apparatus of a medical device operable in a limited amount of time through a deliberate human motion. Although the present embodiments have been described with reference to specific example embodiments, it will be evident that various modifications and changes may be made to these embodiments without departing from the broader spirit and scope of the various embodiments.

In one embodiment, a medical device 150 (e.g., the medical device 150 of FIG. 1, the medical device 650A-N of FIG. 6, a spectroscopic medical device, etc.) includes a power module (e.g., the power module 100, 300, 400, and/or 500 of FIGS. 1, 3, 4, and/or 5) to convert human motion to an electric current. The electric current converted from a deliberate human motion may power the medical device 150 for a limited amount of time.

Figure 1:
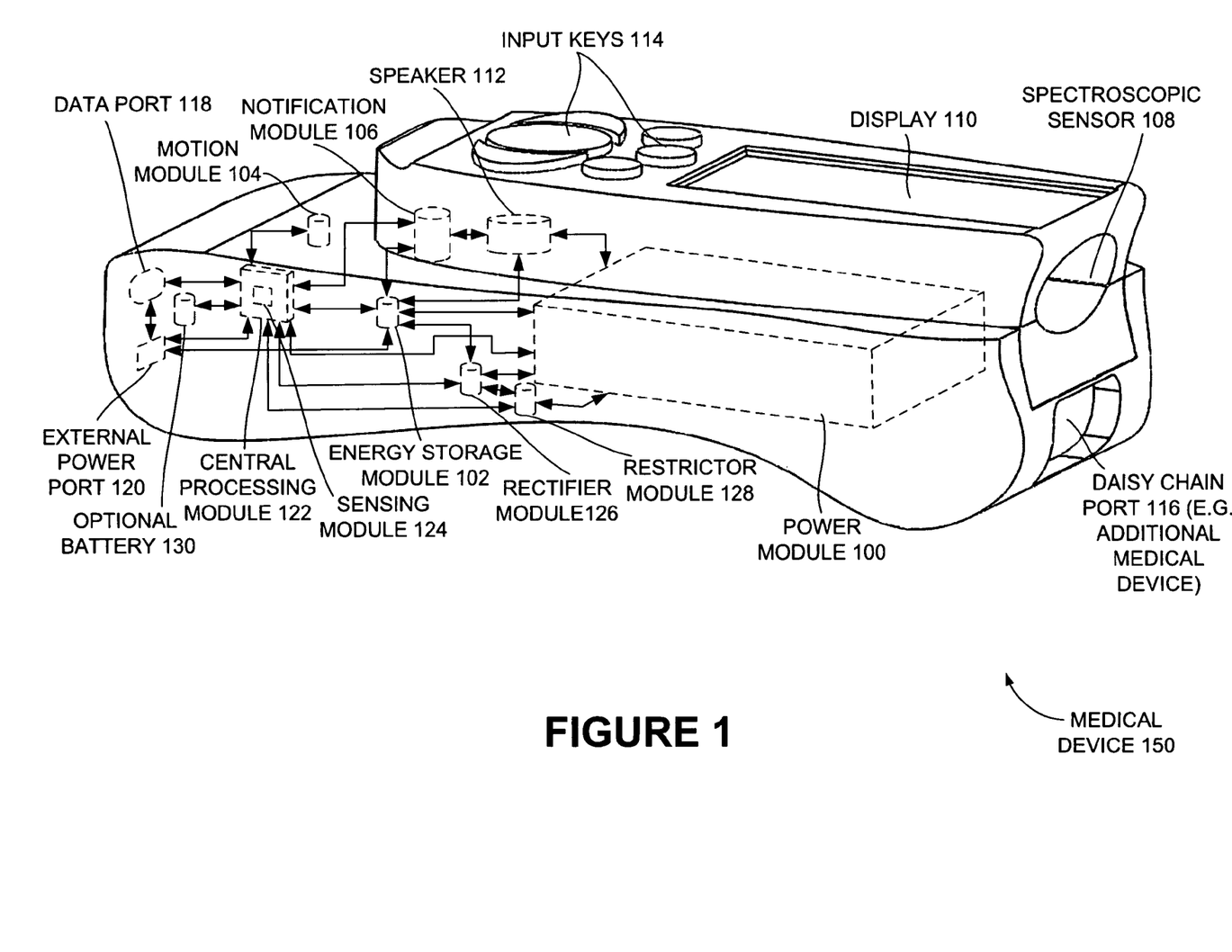
FIG. 1 is a system view of a medical device that includes a power module, an energy storage module, and other various modules communicating with each other, according to one embodiment.

The medical device 150 may be a device (e.g., a pulse oximeter, an electrocardiogram (ECG), an automated external defibrillator (AED), etc.) that may transduce physiological data from a patient for diagnostic and/or therapeutic purposes. The medical device 150 may be a pulse oximeter which may operate on a power supply (e.g., a battery, dynamically generated power, etc.). The medical device 150 may include components to convert and/or store energy which may be required to power the medical device 150. The medical device 150 may be self powered (e.g., through electric current converted by a power module) for processing physiological data and/or to process diagnostic information (a blood oxygen level, a blood chemical presence and/or absence, etc.).

Figure 2:
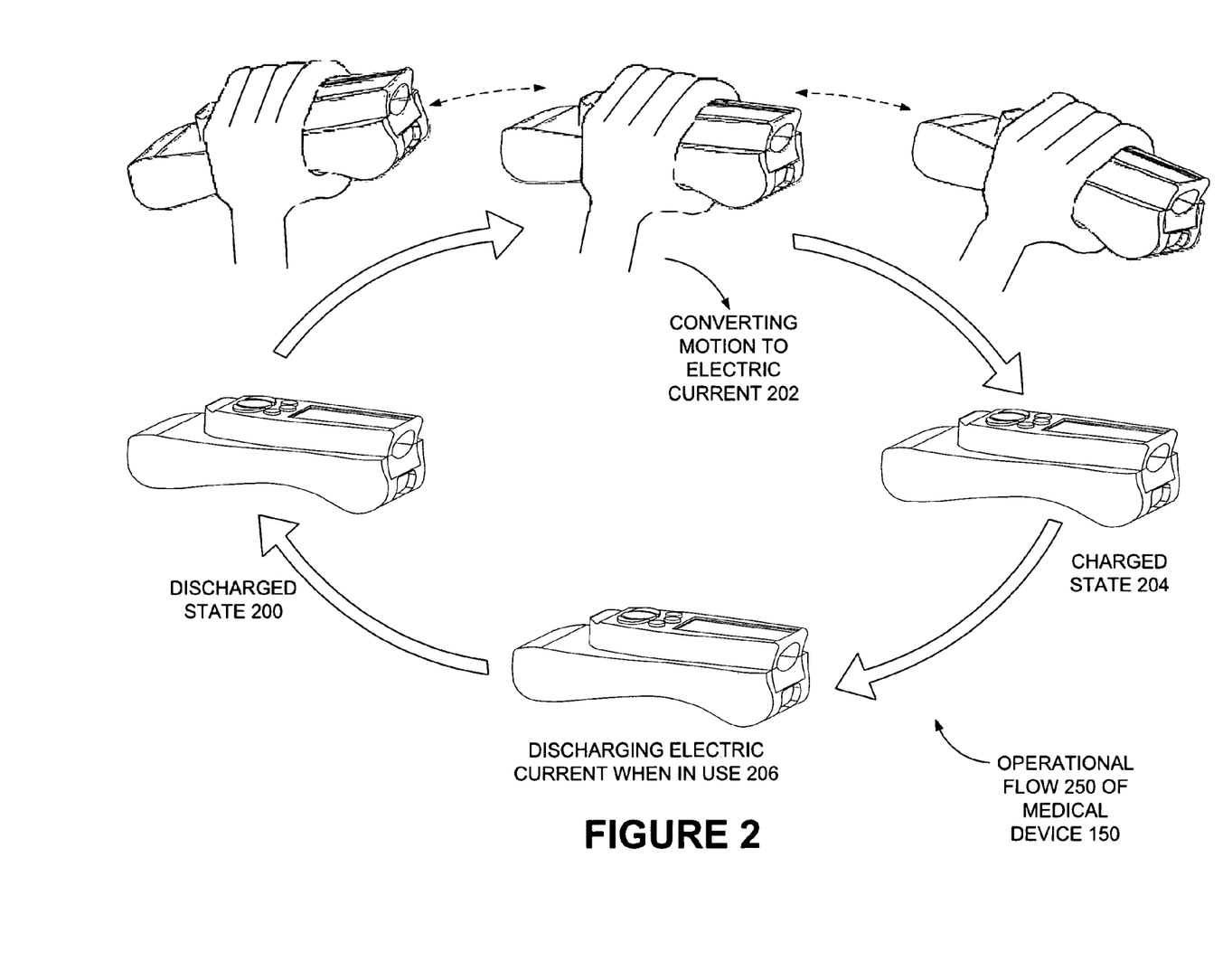
FIG. 2 is a system view of the medical device illustrating a functional cycle (e.g., charging, discharging electric current when in use, etc.), according to one embodiment.

In one embodiment, FIG. 2 illustrates an operational flow 250 of the medical device 150. In particular, FIG. 2 illustrates a discharged state 200, converting motion to electric current 202, a charged state 204, and discharging an electric current when in use 206. In the discharged state 200, the medical device 150 may not have power stored in the device generated by deliberate human motion and/or obtained from another source. Converting motion to electric current 202 may allow a user to generate electric current by deliberately moving (e.g., shaking, oscillating, vibrating, a repeated pressure, etc.) the medical device 150. In the charged state 204, the medical device 150 may retain power generated by a deliberate human motion. Discharging electric current when in use 206 may illustrate using power stored within the medical device 150 to operate the medical device 150 for a limited amount of time (e.g., a single use, several uses, etc.).

In an embodiment, the medical device 150 may generate electric current using the power module (e.g., the power module 100, 300, 400, and/or 500) when the medical device 150 is moved by a deliberate human motion. The power module may be comprised of a magnet and a conductor that move relative to each other to generate an electric current. The electric current may be generated through Faraday's Law of Induction and/or Lenz's law when the medical device 150 is moved, and the magnet and the conductor of the power module may be caused to move in relation to each other. The rectifier module 126 may modify the electric current from the power module (e.g., the power module 100, 300, 400, and/or 500) to be stored in the energy storage module (e.g., capacitance, lithium-ion, lead-acid, and hybrid chemical related devices, etc.).

Figure 3:
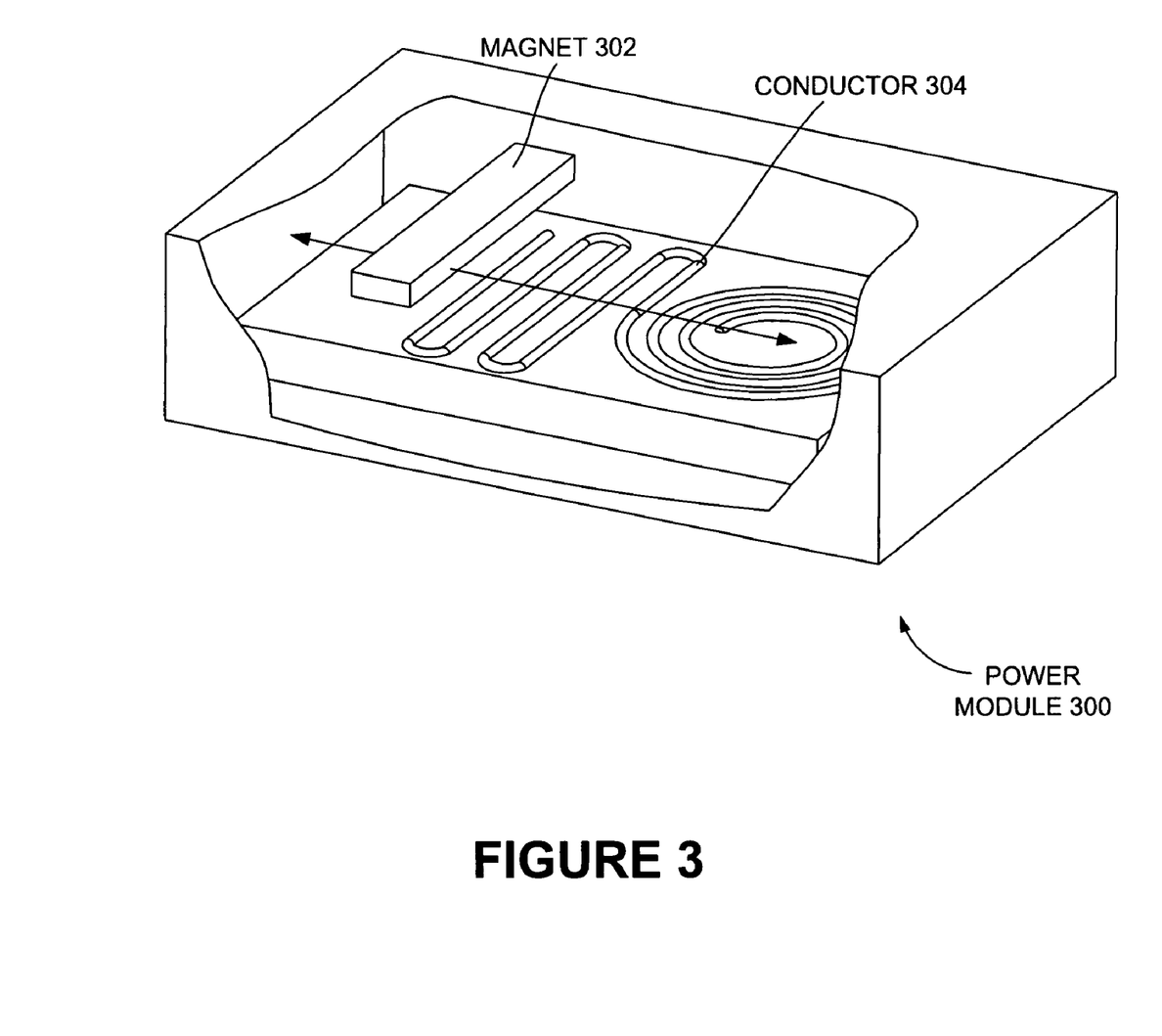
FIG. 3 is a magnified view of the power module, according to one embodiment.

The restrictor module 128 may be a device to prevent the human motion from being converted into the limited use electric current by limiting the motion of the magnet 302 and/or the conductor 304 of the power module 300. In an alternate embodiment, the restrictor module 128 may be comprised of a switch to decouple the power module from the medical device 150.

Figure 4:
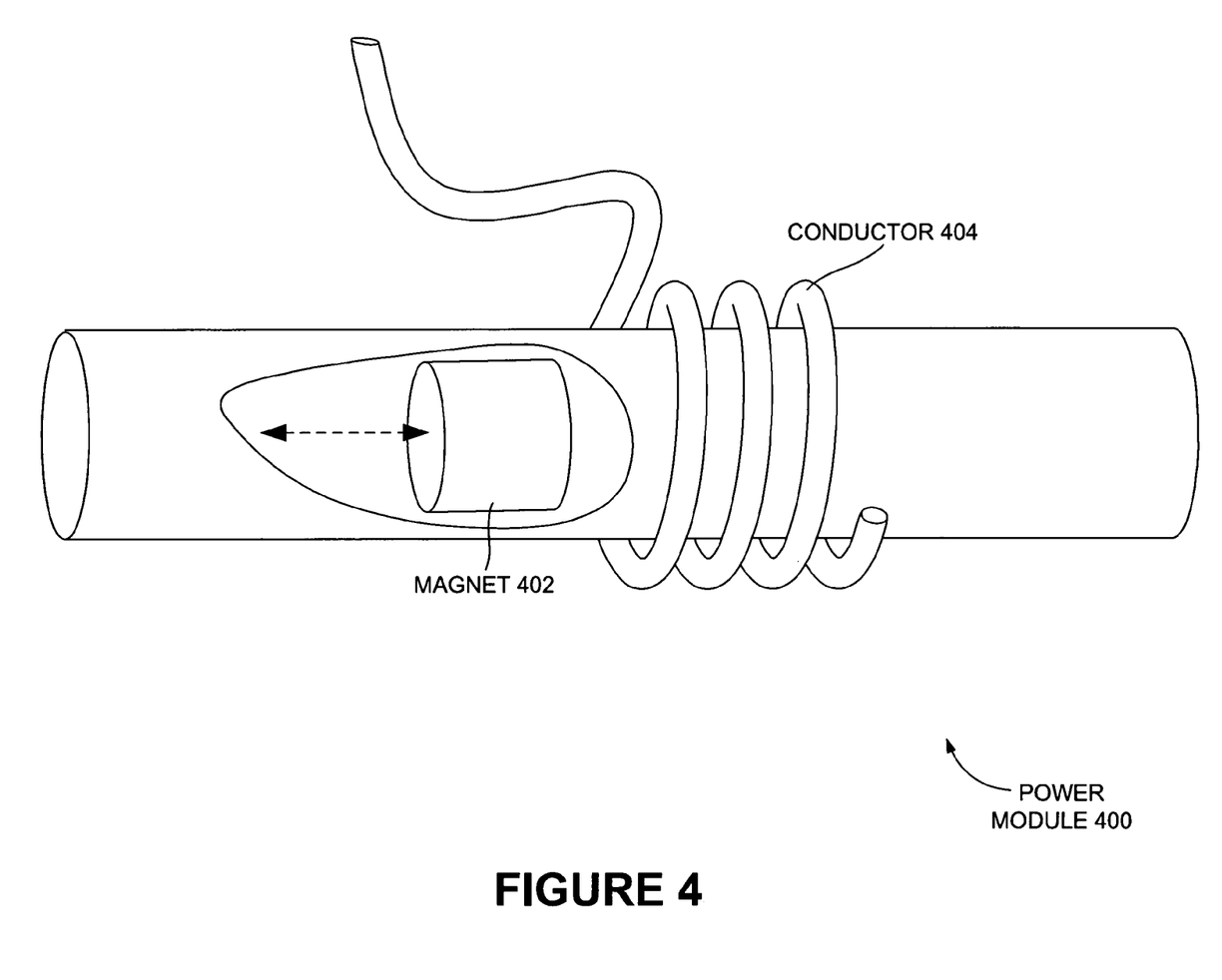
FIG. 4 is a magnified view of the power module, according to another embodiment.
Figure 5:
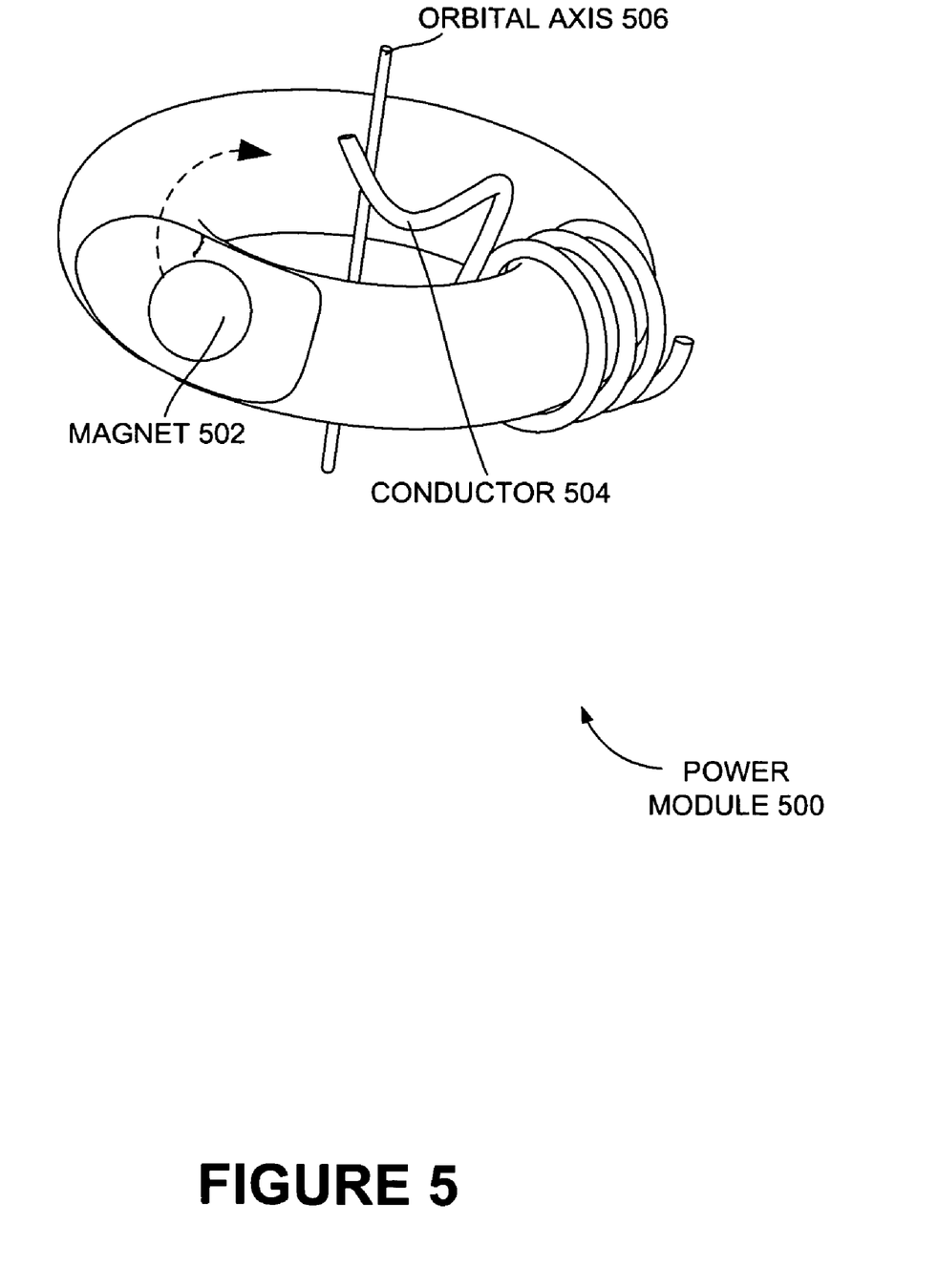
FIG. 5 is a magnified view of the power module, according to yet another embodiment.

Multiple methods and systems may be used by a power module (e.g., the power module 100, 300, 400, and/or 500) to generate an electric current using at least one magnet and at least one conductor, some of which are illustrated in FIGS. 3, 4, and/or 5.

FIG. 3 is a magnified view of one embodiment of the power module (e.g., the power module 100, 400, 500). FIG. 3 illustrates the power module 300, a magnet 302, and a conductor 304. According to one embodiment, FIG. 3 illustrates the manner in which a magnet 302 (e.g., a permanent magnet, a ceramic magnet, an electromagnet, etc.) may be moved in relation to a conductor 304.

The conductor 304 may be comprised of a conductive material (e.g., copper, a doped semiconductor, aluminum, steel, etc.). In addition, the conductor 304 may be oriented in a plane such that a magnet 302 oscillating in a parallel plane may be able to convert the deliberate human motion to the electric current. The conductor 304 may be oriented in a series of rows perpendicular to the path of travel of the magnet 302. The conductor 304 may be oriented in a planar spiral (e.g., a spiral parallel to a surface, a coil parallel to a planar surface, etc.). The conductor 304 may be above a planar surface, below a planar surface, and/or embedded within the planar surface. The conductor 304 may be mechanically coupled to a top and/or a bottom of a planar surface. The conductor 304 and/or the magnet 302 may move relative to the power module 300 and/or each other, such that an electric current is generated within the conductor 304. The change in the magnetic field may be produced by changing the magnetic field strength, moving a magnet toward or away from the coil, moving the coil into or out of the magnetic field, and/or rotating the coil relative to the magnet, etc.

FIG. 4 is a magnified view of the power module 100 of FIG. 1, according to one embodiment. FIG. 4 illustrates the power module 400, a magnet 402, and a conductor 404. FIG. 4 illustrates the manner in which a magnet 402 (e.g., a permanent magnet, a ceramic magnet, an electromagnet, etc.) may be moved in relation to a conductor 404. The conductor 404 may be comprised of a conductive material (e.g., copper, a doped semiconductor, aluminum, steel, etc.). In addition, the conductor 404 may be shaped to form a coil of the conductor 404, such that the magnet is able to oscillate through the coil of the conductor to convert the deliberate human motion to an electric current. The motion of the magnet 402 in relation to the conductor 404 may be used to generate electric current. The magnet 402 may move in relation to the conductor 404 when the medical device is moved by a deliberate human motion.

FIG. 5 is yet another magnified view of the power module 100 of FIG. 1, according to one embodiment. FIG. 5 illustrates the power module 500, a magnet 502, a conductor 504, and an orbital axis 506. The magnet 502 (e.g., a permanent magnet, a ceramic magnet, an electromagnet, etc.) and/or the conductor 504 (e.g., copper, a doped semiconductor, aluminum, steel, etc.) may rotate with respect to the orbital axis 506.

The conductor 504 may be comprised of a conductive material (e.g., copper, a doped semiconductor, aluminum, steel, etc.). In addition, the conductor 504 may be shaped to form a coil of the conductor 504, such that the magnet is able to oscillate through the coil of the conductor to convert the deliberate human motion to an electric current. The motion of the magnet 502 in relation to the conductor 504 may be used to generate electric current. The magnet 502 may move in relation to the conductor 504 when the medical device is moved by a deliberate human motion.

Figure 8:
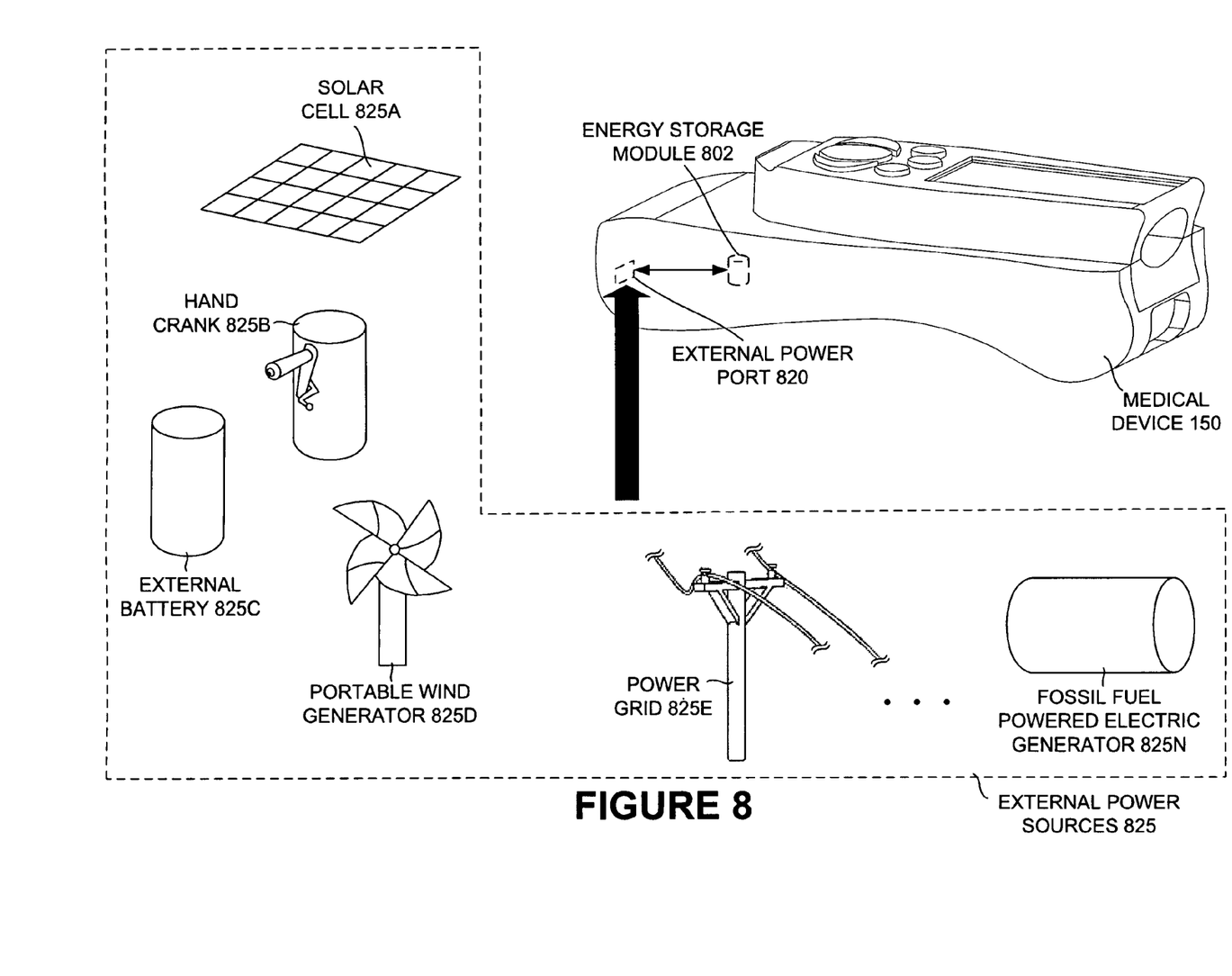
FIG. 8 is a system view of a medical device and multiple power sources, according to one embodiment.

In another embodiment, the electric current generated by the power module (e.g., the power module 100, 300, 400, and/or 500) may be stored in an energy storage module 102 (e.g., a battery, a capacitor, a hybrid device with capacitance, a device that may be used in place of battery, etc.). The energy storage module 102 may accumulate power from the electric current generated by the power module when a deliberate human motion moves the medical device 150. The energy storage module 102 may discharge electric current to operate the medical device 150 for a limited amount of time. The power of the electric current generated by deliberate human motion may be stored in a capacitance within the energy storage module 102. The energy storage module (e.g., the energy storage module 102 and/or 802) may also store the electric current from external sources of power, such as a solar cell 825A, a hand crank 825B, an external battery 825C, a portable wind generator 825D, a power grid 825E, and a fossil fuel powered electric generator 825N or other sources of power, as illustrated in FIG. 8.

In another embodiment, the medical device 150 may be comprised of a motion module 104. The motion module 104 may sense whether a deliberate human motion (e.g., a shaking, an oscillation, etc.) is convertible to an electric current to power the medical device 150. Intentional human actions may be differentiated from unintended or mechanical motions by the motion module 104 based on a direction of motion, a threshold amplitude of motion, a frequency of motion, a button, a switch, a device state and/or a user command.

The motion module 104 may be comprised of a device (e.g., a sensor, an accelerometer, a gyroscope, a solenoid, etc.) to sense whether a human motion may be convertible to power the medical device 150. The motion module 104 may determine whether the power is convertible by observing the motion of an object (e.g., a physical object in the medical device 150, a magnet 302, 402, and/or 502, a mechanical sensor component within the motion module, etc.). The motion module 104 may be comprised of the components of the power module 100, and the motion module 104 may not have parts that are distinct from the power module 100.

In one embodiment, the medical device 150 may lack a motion module 104. In a further embodiment, the motion module 104 may use a moveable part of the power module 100 to sense whether the deliberate human motion may be convertible to the electric current to power the medical device. The moveable part of the power module 100 used by the motion module 104 may be a magnet. In one embodiment, the components of the motion module 104 are comprised of components of the power module 100. In another embodiment, the components of the motion module 104 are distinct from the components of the power module 100.

In another embodiment, the medical device 150 may be comprised of a central processing module 122, a sensing module 124, a spectroscopic sensor 108, a display 110, input keys 114, a daisy chain port 116, a data port 118, a notification module 106, a speaker 112, and/or an external power port 120.

The central processing module 122 may control the function and process data of the spectroscopic sensor 108. The central processing module 122 may be coupled to the energy storage module 102, the motion module 104, the notification module 106, the data port 118, the external power port 120, the sensing module 124, and/or the optional battery 130. The sensing module 124 (e.g., a current meter, a voltmeter, a magnetometer, an oscillation counter, a timer, etc.) may determine whether the threshold amount of power needed to operate the medical device 150 has been generated and stored.

Figure 7:
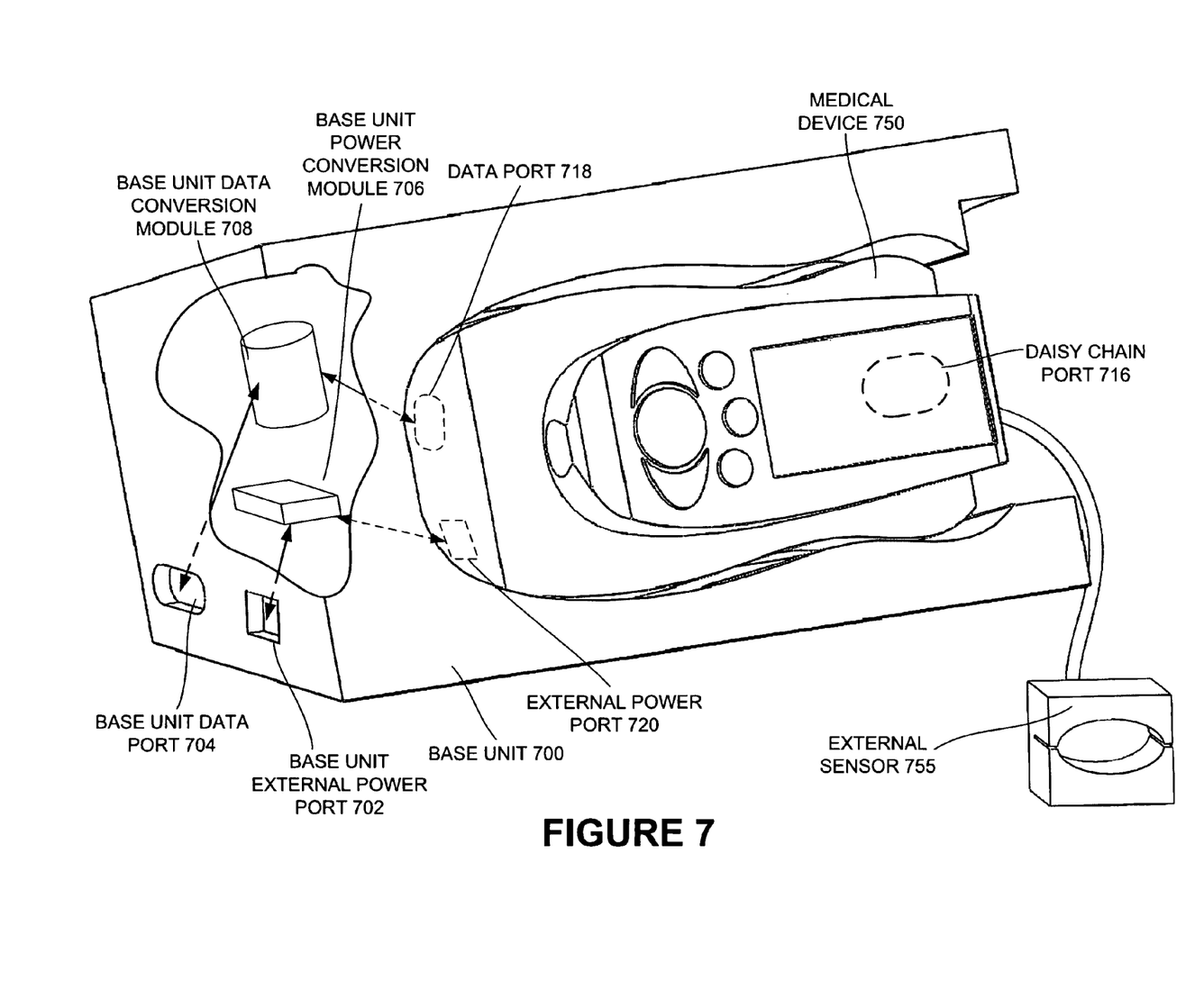
FIG. 7 is a magnified view of a medical device coupled to a base unit, according to another embodiment.

The central processing module 122 may process input signals (e.g., signals from the spectroscopic sensor 108 and/or signals from the external sensor 755, signals from the input keys 114). The input signals may contain patient data (e.g., pulse oximetry data, heart rate data, glucose readings, etc.). In addition, the central processing module 122 may process control signals from the input keys 114 to manage the medical device 150.

The spectroscopic sensor 108 (e.g., a pulse oximeter and/or a glucometer) may perform an oxygen saturation reading, a heart rate reading and/or a blood glucose level reading when powered for a limited amount of time. In one embodiment, the spectroscopic sensor 108 may be powered by the electric current converted by the power module (e.g., the power module 100, 300, 400, and/or 500).

The display 110 (e.g., an LED, an LCD screen, a series of LED's, an OLED display etc.) may show the results of a reading by the spectroscopic sensor 108, a power status of the energy storage module 102, a notification module 106 output, a central processing module 122 output, and/or a response to a use of input keys 114.

The input keys 114 may provide a means for a user to communicate with the central processing module 122. The input keys 114 may allow a user to begin a reading by the spectroscopic sensor 108, and/or to control a display 110 output.

The daisy chain port 116 may allow an additional medical device (e.g., the medical device 650A-N of FIG. 6, the external sensor 755 of FIG. 7, etc.) to be connected to the medical device 150. The daisy chain port 116 may be coupled to the central processing module 122. The data port 118 (e.g., a USB port, a socket, a DB9 type connector, etc.) may allow the medical device 150 to connect another device. The data port 118 may be an interface to transfer medical data (e.g., oxygen saturation, glucose readings, etc.) to other medical devices (e.g., a low-cost computer, data processing devices, a modular medical device system, etc.) for further processing.

The notification module 106 may use an audible tone, a vibration, and/or a visual signal to notify a user that the electric current converted from the deliberate human motion has reached a threshold level. The notification module 106 may be comprised of a tone generator, an LED, a vibration generator. The notification module may use the speaker 112 and/or the display 110 to notify the user that a threshold amount of electric current has been stored. The notification module may be coupled with the central processing module. The speaker 112 may be an electromagnetic device that converts one form of energy to another form (e.g., electrical signal to sound, etc.).

The external power port 120 may allow an external power source to provide electric current to the medical device 150. In one embodiment, the external power port 120 may be coupled to a solar cell 825A, a hand crank 825B, an external battery 825C, a portable wind generator 825D, a power grid 825E, a fossil fuel powered electric generator 825N, and/or other sources of power, as illustrated in FIG. 8.

In an additional example embodiment, the optional battery 130 may be coupled with the energy storage module 102 to store power from the electric current converted by the human motion. The optional battery 130 may also store power provided by external power sources 825.

Figure 6:
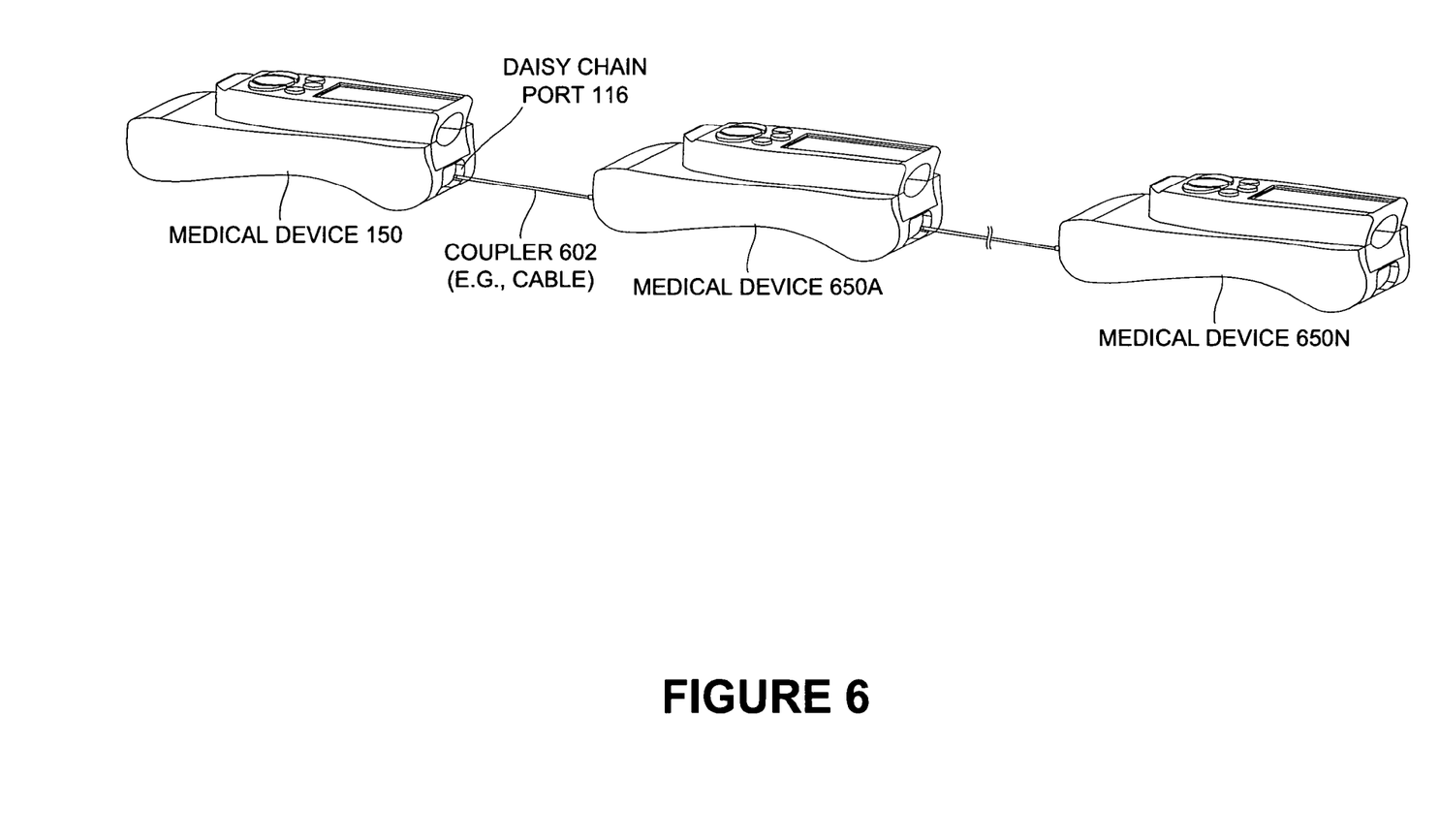
FIG. 6 is a system view of multiple medical devices coupled to each other, according to one embodiment.

FIG. 6 is a schematic view illustrating multiple medical devices coupled to each other. The medical device 150 may be connected to additional medical devices 650A-N with a coupler 602 (e.g., a cable). The coupler 602 may be connected to the daisy chain port 116 of the medical device 150. The coupler 602 may be connected to a data port 118 of a medical device (e.g., the medical device 150, the medical devices 650A-N).

FIG. 7 is an alternate schematic view of the medical device 150, according to one embodiment. Particularly, FIG. 7 illustrates the medical device 750, the daisy chain port 716, the base unit 700, the base unit external power port 702, the base unit data port 704, the base unit power conversion module 706, the base unit data conversion module 708, an external sensor 755, the data port 718, and the external power port 720, according to one embodiment.

The base unit 700 may be a device (e.g., a holder, a converter, etc.) that is compatible with the medical device (e.g., the medical device 150 and/or 750). The base unit 700 may be used to provide power supply to the medical device 750, and it may transfer data between an external device and the medical device 750. The base unit external power port 702 may provide power to the medical device 750. The base unit data port 704 may be an interface to enable the base unit 700 to connect with another medical device (e.g., an external display, an external processor, an external memory, a hard drive, etc.). The base unit power conversion module 706 may convert electrical power from an external source (e.g., wind power, hand crank power, external mains electricity, etc.) to power the medical device 750. The base unit data conversion module 708 may convert data (e.g., digital signals of various packet sizes and amplitudes, etc.) from the medical device 750 to an alternate data format (e.g., digital signals of differing packet sizes and amplitudes, etc.). The base unit data conversion module 708 may further convert data from the other external devices that may be connected to the medical device 750 and/or the base unit 700.

In an example embodiment, FIG. 7 illustrates the medical device 750 connected to the base unit 700. The base unit 700 may include the base unit external power port 702, the base unit data port 704, the base unit power conversion module 706, the base unit data conversion module 708 and other supporting devices (e.g., components). The base unit may be designed to make the medical device 750 universally compatible. The base unit data port 704 may be compatible with the data port 718 of the medical device 750. The base unit external power port 702 may be compatible with the external power port 720 of the medical device 750. The base unit data conversion module 708 may act as an interface between the data port 718 of the medical device 750 and the base unit data port 704. The base unit power conversion module 706 may act as an interface between the external power port 720 of the medical device 750 and the base unit external power port 702. The base unit data conversion module 708 and the base unit power conversion module 706 may increase the scope of the use of the medical device 750 in connection with other devices.

The base unit 700 may receive power from external sources for the medical device 750. The power may be transmitted from the base unit 700 to the medical device. The base unit may function as an interface between the medical device 750 and the other external devices. The base unit 700 may also enable communication of data between the medical device 750 and the external devices. The base unit 700 may hold the medical device 750 in a preferred orientation in space to facilitate interaction with the user interface (e.g., the display 110, the input keys 114, etc.) by the user.

FIG. 8 is a system view of the medical device 150 that may use an alternative source of energy (e.g., wind power, solar power, external batteries, etc.) according to one embodiment. Particularly, FIG. 8 illustrates the medical device 150, the energy storage module 802, external power sources 825, a solar cell 825A, a hand crank 825B, an external battery 825C, a portable wind generator 825D, a power grid 825E, a fossil fuel powered electric generator 825N, according to one embodiment.

The external power sources 825 (e.g., a power grid 825E, portable wind generator 825D, etc.) may provide power supply to the medical device 150 when required. The solar cell 825A (e.g., a photovoltaic cell) may be a device to convert solar energy (e.g., light energy) to an electric current (e.g., photovoltaic effect). The solar cell 825A may provide an alternate source of an electric current to operate the medical device 150. The hand crank 825B may convert rotary motion (e.g., mechanical energy) to an electric current. The hand crank 825B may include a handle or arm attached at right angles to a shaft. The hand crank 825B may be used as an optional source of an electric current to operate the medical device 150.

The external battery 825C may be an array of electrochemical cells for electricity storage. The external battery 825C may be used as an optional source of electric current to operate the medical device 150. The portable wind generator 825D may be a device (e.g., including rotating vanes) to convert the kinetic energy in wind into an electric current. The portable wind generator 825D may be used as an optional source of electricity to operate the medical device 150. The power grid 825E may be commercially available power from a power grid which allows the medical device 150 to function. The fossil fuel powered electric generator 825N may generate an electric current by burning a fossil fuel (e.g., petrol, Gasoline, diesel, etc.). The base unit power conversion module 706 may communicate with the external power sources 825 through the base unit power port 702. In one embodiment, the energy storage module 102 and/or the optional battery 130 may also be able to store the electricity from the external power sources 825 to allow the medical device 150 to continue to operate should it be removed from the base unit 700 or should the power supplied by the external power sources 825 be temporarily interrupted.

Figure 9:
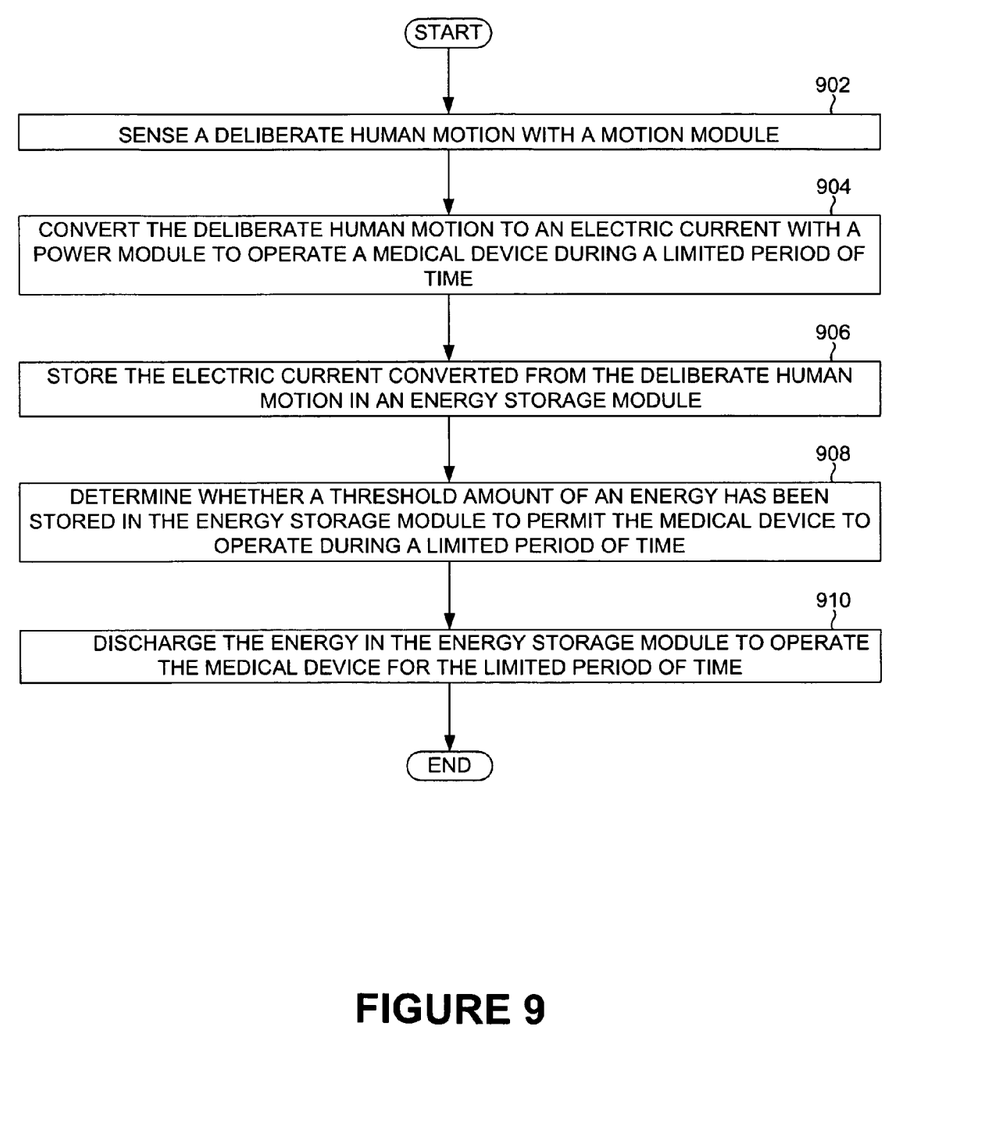
FIG. 9 is a process flow of sensing a deliberate human motion with a motion module and converting the deliberate human motion to an electric current, according to one embodiment.

FIG. 9 is a process flow of using the medical device (e.g., the medical device 150 of FIG. 1) to convert a deliberate human motion to electric current to power the medical device for a limited period of time, according to one embodiment. In operation 902, a deliberate human motion may be sensed with the motion module 104. In operation 904, the deliberate human motion may be converted to an electric current with a power module (e.g., the power module 100, 300, 400, and/or 500) to operate the medical device 150 during a limited period of time. In operation 906, the electric current converted from the deliberate human motion may be stored in an energy storage module (e.g., the energy storage module 102). In operation 908, it may be determined by the sensing module 124 whether a threshold amount of energy has been stored in the energy storage module 102 to permit the medical device 150 to operate during a limited period of time. In operation 910, the energy in the energy storage module 102 may be discharged to operate the medical device 150 for a limited period of time.

Figure 10:
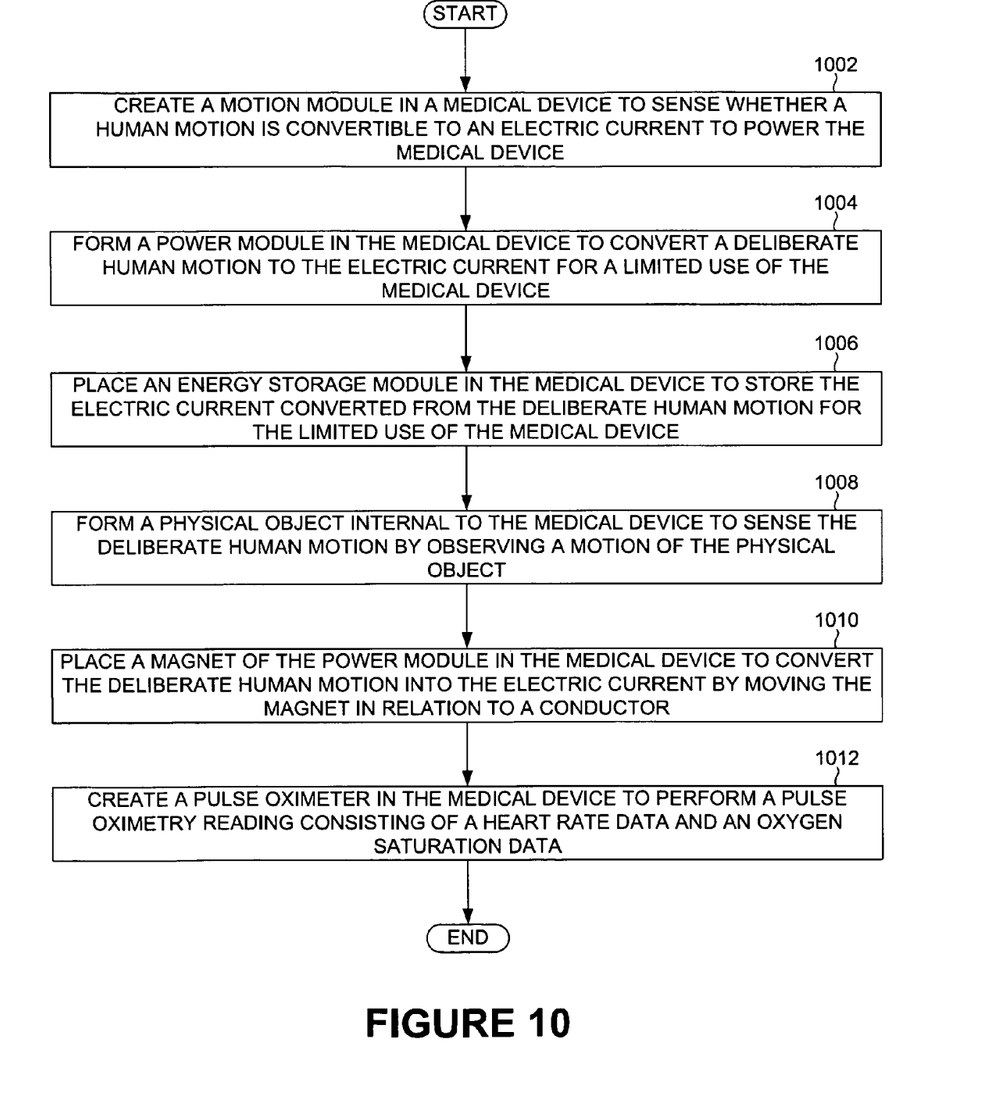
FIG. 10 is a process flow of forming components of the medical device to convert a deliberate human motion to an electric current to be used to perform a pulse oximetry reading, according to one embodiment.

FIG. 10 is a process flow of forming components of the medical device 150, according to one embodiment. In operation 1002, a motion module (e.g., the motion module 104) may be created in the medical device 150 to sense whether a human motion is convertible to an electricity (e.g., an electric current, a charge, a voltage, an electric potential, etc.) to power the medical device 150. In operation 1004, the power module (e.g., the power module 100, 300, 400, and/or 500) may be formed in the medical device 150 to convert a deliberate human motion to the electricity for a limited use of the medical device 150. In operation 1006, an energy storage module (e.g., the energy storage module 102 of FIG. 1) may be placed in the medical device 150 to store the electricity converted from the deliberate human motion for the limited use of the medical device 150. In operation 1008, a physical object may be formed internal to the medical device 150 to sense the deliberate human motion by observing a motion of the physical object. In operation 1010, a magnet (e.g., the magnet 302, 402, and/or 502) of the power module (e.g., the power module 100, 300, 400, and/or 500) may be placed in the medical device 150 to convert the deliberate human motion into the electric current by moving the magnet (e.g., the magnet 302, 402, and/or 502) in relation to a conductor (e.g., the conductor 304, 404, and/or 504). In operation 1012, a pulse oximeter may be created in the medical device 150 to perform a pulse oximetry reading consisting of a heart rate data and/or an oxygen saturation data.

Although the present embodiments have been described with reference to specific example embodiments, it will be evident that various modifications and changes may be made to these embodiments without departing from the broader spirit and scope of the various embodiments. For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated (ASIC) circuitry and/or in Digital Signal Processor (DSP) circuitry).

Particularly, the power module 100, the energy storage module 102, the motion module 104, the notification module 106, the central processing module 122, the rectifier module 126, the sensing module 124, the restrictor module 128, the base unit power conversion module 706, the base unit data conversion module 708, the external power sources 825, of FIG. 1-10 may be enabled using software and/or using transistors, logic gates, and electrical circuits (e.g., application specific integrated ASIC circuitry) such as a power circuit, a energy storage circuit, a motion circuit, a notification circuit, a signal processing circuit, a rectifier circuit, a power sensing circuit, a restrictor circuit, a base unit power conversion circuit, a base unit conversion circuit, a external power circuit, and other circuits using one or more of the technologies described herein.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:
1. A medical device comprising:
  a sensor configured to sense physiological data from a patient;
  a power module configured to convert deliberate human motion to an electric current which enables the medical device to operate during a limited period of time;
  the power module including a conductor and a magnet configured to convert the deliberate human motion to the electric current by moving through a fixed path in relation to the conductor, wherein the deliberate human motion comprises a shaking motion of the power module by a hand of a user that causes the magnet of the power module to oscillate in relation to the conductor and to convert the deliberate human motion to an electric current;

a power sensing module configured to determine whether a threshold amount of energy has been generated and stored, the threshold amount of energy being sufficient to sense the physiological data for the limited period of time;

an energy storage module configured to store electric current converted from the deliberate human motion, the energy storage module coupled with the sensor so as to power the sensor after the shaking motion has stopped and throughout the limited period of time; wherein the energy storage module and power module are configured for repeated use after the limited period of time has expired so as to facilitate sensing additional physiological data for another limited period of time by again shaking the power module with the hand of the user;

a user interface operatively coupled with the sensor, wherein the sensor, power module, power sensing module, and energy storage module are mounted to a housing and configured to be shaken by the hand of the user with the housing during the deliberate human motion; and a base station unit that, when in use, releasably supports and fixedly orients the interface of the medical device toward the user during sensing of the physiological data;

and wherein the medical device is powered by electrical current generated by the shaking motion.

2. The medical device of claim 1 further comprising a motion module to sense whether a deliberate human motion is convertible to an electric current to power the medical device, and a sensor of the motion module to sense whether the deliberate human motion is convertible to the electric current by permitting a physical object to oscillate.

3. The medical device of claim 1 further comprising a coil oriented in a plane such that the magnet oscillating in a parallel plane is able to convert the deliberate human motion to the electric current.

4. The medical device of claim 1 further comprising a coil of the conductor of the power module such that the magnet is able to oscillate through the coil of the conductor to convert the deliberate human motion to an electric current.

5. The medical device of claim 1 further comprising an axis of the power module such that the magnet is able to orbit the axis with relation to a fixed conductor to convert the deliberate human motion to an electric current.

6. The medical device of claim 1 wherein operation of the medical device during the limited period of time is a single use of the medical device such that it is usable one time before discharging the energy storage module.

7. The medical device of claim 6 wherein a power converted from the deliberate human motion is stored in a capacitance within the energy storage module.

8. The medical device of claim 1 further comprising a spectroscopic sensor powered by the electric current from the deliberate human motion, wherein the spectroscopic sensor is at least one of a pulse oximeter and a glucometer, and wherein operating the medical device performs at least one of an oxygen saturation reading, a heart rate reading and a glucometer reading.

9. The medical device of claim 8 further comprising a port for another sensor powered for the limited period of time by an energy converted from the deliberate human motion.

10. The medical device of claim 9 further comprising a notification module using at least one of an audible tone, a vibration, and a visual signal to notify a user that the electric current converted from the deliberate human motion has reached a threshold level.

11. The medical device of claim 9 further comprising a display powered by the electric current from the deliberate human motion to display information associated with data captured during the limited period of time the medical device is operational.

12. The medical device of claim 11 further comprising a rectification module to modify the electric current to be stored in the energy storage module.

13. The medical device of claim 12 further comprising:
a restrictor module to prevent the deliberate human motion from being converted into the electric current by limiting a motion of at least one of a magnet and a conductor; and
a base unit to provide a constant electric current to allow continuous use of the medical device and to hold the medical device in a preferred position.

14. The medical device of claim 13 wherein the energy storage module is also able to store the electric current from at least one of a hand crank, an external battery, a solar cell, a commercially available mains power, a fossil fuel powered generator, and a wind generator to operate the medical device during the limited period of time.

* * * * *